(12) United States Patent
Marcus et al.

(10) Patent No.: US 12,377,063 B2
(45) Date of Patent: Aug. 5, 2025

(54) COMBINATION THERAPIES FOR MANAGING CANCER

(71) Applicant: Emory University, Atlanta, GA (US)

(72) Inventors: Adam Marcus, Atlanta, GA (US); Malathy Shanmugam, Atlanta, GA (US)

(73) Assignee: Emory University, Atlanta, GA (US)

( * ) Notice: Subject to any disclaimer, the term of this patent is extended or adjusted under 35 U.S.C. 154(b) by 813 days.

(21) Appl. No.: 17/626,346

(22) PCT Filed: Jul. 10, 2020

(86) PCT No.: PCT/US2020/041565
§ 371 (c)(1),
(2) Date: Jan. 11, 2022

(87) PCT Pub. No.: WO2021/007499
PCT Pub. Date: Jan. 14, 2021

(65) Prior Publication Data
US 2022/0265584 A1    Aug. 25, 2022

Related U.S. Application Data

(60) Provisional application No. 62/872,923, filed on Jul. 11, 2019.

(51) Int. Cl.
*A61K 31/192* (2006.01)
*A61K 31/155* (2006.01)
(Continued)

(52) U.S. Cl.
CPC .......... *A61K 31/155* (2013.01); *A61K 31/192* (2013.01); *A61K 31/405* (2013.01); *A61K 45/06* (2013.01); *A61P 35/00* (2018.01)

(58) Field of Classification Search
CPC .. A61K 31/155; A61K 31/192; A61K 31/405; A61K 45/06; A61P 35/00
See application file for complete search history.

(56) References Cited

U.S. PATENT DOCUMENTS

| 6,613,310 B1 | 9/2003 | Campbell |
| 7,470,428 B2 | 12/2008 | Kuchroo |

(Continued)

FOREIGN PATENT DOCUMENTS

| WO | 2004004658 | 1/2004 |
| WO | 2005060951 | 7/2005 |

(Continued)

OTHER PUBLICATIONS

Tylicki et al., Can J Microbiol, 2005, 51:833-839 (Year: 2005).*
(Continued)

*Primary Examiner* — Andrew D Kosar
*Assistant Examiner* — Jonathan D Mahlum
(74) *Attorney, Agent, or Firm* — Emory Patent Group

(57) ABSTRACT

Disclosed herein are methods of managing cancer and tumor growth. This disclosure relates to methods of treating cancer comprising administering a combination of chemotherapy agents, wherein a first chemotherapy agent is capable of inhibiting oxidative phosphorylation of pyruvate and a second chemotherapy agent is capable of inhibiting glucose metabolism. In certain embodiments, the first and second chemotherapy agents are administered in combination with an additional chemotherapy agent.

2 Claims, 12 Drawing Sheets

(51) Int. Cl.
  A61K 31/405    (2006.01)
  A61K 31/409    (2006.01)
  A61K 31/44     (2006.01)
  A61K 31/4709   (2006.01)
  A61K 31/506    (2006.01)
  A61K 31/5685   (2006.01)
  A61K 45/06     (2006.01)
  A61P 35/00     (2006.01)

(56) References Cited

U.S. PATENT DOCUMENTS

| | | | |
|---|---|---|---|
| 8,119,684 B2 | 2/2012 | Yeh | |
| 2002/0198264 A1* | 12/2002 | Gerson | A61K 31/513 514/645 |
| 2003/0139331 A1* | 7/2003 | Martin | A61K 31/7076 514/19.3 |
| 2004/0077601 A1 | 4/2004 | Adams | |
| 2009/0324682 A1 | 12/2009 | Popowski | |
| 2012/0136007 A1 | 5/2012 | Mootha | |
| 2019/0195858 A1 | 6/2019 | Marcus | |

FOREIGN PATENT DOCUMENTS

| | | | |
|---|---|---|---|
| WO | WO2011017809 | * | 2/2011 |
| WO | 2015091428 | | 6/2015 |
| WO | WO2017180581 | * | 10/2017 |
| WO | WO2019070777 | * | 4/2019 |
| WO | WO2019204251 | * | 10/2019 |

OTHER PUBLICATIONS

Yip et al., Mol Cancer Ther, 2006, 5:2234-2240 (Year: 2006).*
Bhardwaj et al., Tumor Biol, 2012, 33:1021-1030 (Year: 2012).*
Denise et al., Oncotarget, 2015, 6:41706-41721 (Year: 2015).*
Alistar et al., Lancet Oncol, 2017, 18:770-778 (Year: 2017).*
Beloueche-Babari et al., Cancer Res, 2017, 77:5913-5924 (Year: 2017).*
Shirmanova et al., Sci Rep, 2017, 7:8911 (Year: 2017).*
Cesi et al., Mol Cancer, 2017, 16:102 (Year: 2017).*
Bagri, VCU Undergraduate Research Posters, 2018, Poster 251 (Year: 2018).*
Mungo et al., Int J Mol Sci, 2018, 19:3550 (Year: 2018).*
Su et al., Oncol Lett, 2019, 18:5663-5672 (Year: 2019).*
Sawayama et al., Cancer Sci, 2019, 110:1705-1714 (Year: 2019).*
Liu et al., Cancer Sci, 2019, 110:2493-2506 (Year: 2019).*
Toth et al., Mol Cancer Ther, 2021, 20:3-10 (Year: 2021).*
Peng et al., Cell Commun Signal, 2022, 20:194 (Year: 2022).*
Liu et al., Cancer Manag Res, 2023, 15:957-975 (Year: 2023).*
Maurer et al., Am J Physiol Cell Physiol, 2023, 325:C1131-C1143 (Year: 2023).*
Chen et al., J Zhjiang Univ-Sci B (Biomed & Biotechnol), 2023, 24:397-405 (Year: 2023).*
Bajpai et al., Curr Opin Oncol, 2018, 30:338-344 (Year: 2018).*
Maki et al., Oncol Rep, 2013, 29:133-140 (Year: 2013).*
Koch et al., Oncotarget, 2015, 6:32748-32760 (Year: 2015).*
Niemi et al., PLOS One, 2013, 8:e53803 (Year: 2013).*
Bader et al. Mitochondrial pyruvate import is a metabolic vulnerability in androgen receptor-driven prostate cancer, Nature Metabolism, vol. 1, pp. 70-85 (2019).
Bryant et al. Combination of ERK and autophagy inhibition as a treatment approach for pancreatic cancer, Nature Medicine, vol. 25, pp. 628-640 (2019).
Burrell et al. The causes and consequences of genetic heterogeneity in cancer evolution, Nature, vol. 501, pp. 338-345 (2013).
Chen et al., HMGB1 Controls Liver Cancer Initiation through YAP-dependent Aerobic Glycolysis, Hepatology, 2018, 67(5): 1823-1841.
Commander et al. Subpopulation targeting of pyruvate dehydrogenase and GLUT1 decouples metabolic heterogeneity during collective cancer cell invasion, Nature Communications, vol. 11, Article No. 1533 (2020).
Graber et al. Oral Disinfectants Inhibit Protein-Protein Interactions Mediated by the Anti-Apoptotic Protein Bcl-xL and Induce Apoptosis in Human Oral Tumor Cells, Angew. Chem. Int. Ed., 2013, 52, 4487-4491.
Hsu et al. Identification of approved and investigational drugs that inhibit hypoxia-inducible factor-1 signaling, Oncotarget. 2016, 7(7): 8172-8183.
Koch et al. Glucose transporter isoform 1 expression enhances metastasis of malignant melanoma cells, Oncotarget. 2015, 6(32): 32748-32760.
Konen et al. Attacking the SAGA of tumor heterogeneity: The development of a novel technique to provide spatiotemporal genomic profiling of rare cancer cells, In: Proceedings of the AACR Special Conference on Translation of the Cancer Genome; Feb. 7-9, 2015; San Francisco, CA. Philadelphia (PA): AACR; Cancer Res 2015, 75(22 Suppl 1):Abstract nr A1-18.
Konen et al. Image-guided genomics of phenotypically heterogeneous populations reveals vascular signalling during symbiotic collective cancer invasion, Nature Communications, vol. 8, Article No. 15078 (2017).
Kopitz et al. Pharmacological characterization of BAY-876, a novel highly selective inhibitor of glucose transporter (GLUT)-1 in vitro and in vivo, Cancer Res (2016) 76 (14_Supplement): 4746.
Li et al. A Multicenter Double-blind Phase II Study of Metformin With Gefitinib as First-line Therapy of Locally Advanced NoneSmall-cell Lung Cancer, Clinical Lung Cancer, 2016, vol. 18, No. 3, 340-3.
Liao et al., Curcumin inhibits lung cancer invasion and metastasis by attenuating GLUT1/MT1-MMP/MMP2 pathway, Int J Clin Exp Med, 2015, 8(6):8948-8957.
Lo et al. Computational Cell Cycle Profiling of Cancer Cells for Prioritizing FDA Approved Drugs with Repurposing Potential, Scientific Reports, vol. 7, Article No. 11261 (2017).
Ma et al., Ovarian Cancer Relies on Glucose Transporter 1 to Fuel Glycolysis and Growth: Anti-Tumor Activity of BAY-876, Cancers, 2019, 11, 33.
Mamouei et al. Alexidine dihydrochloride has broad spectrum activities against diverse fungal pathogens. mSphere, 2018, 3(5):e00539-18.
Niemi et al., Downregulation of the Mitochondrial Phosphatase PTPMT1 Is Sufficient to Promote Cancer Cell Death Downregulation of the Mitochondrial Phosphatase PTPMT1 Is Sufficient to Promote Cancer Cell Death, PLoS One, 2013, 8(1): e53803.
Oppermann et al. Pyruvate attenuates the anti-neoplastic effect of carnosine independently from oxidative phosphorylation, Oncotarget, 2016, vol. 7, (No. 52), pp. 85848-85860.
Siebeneicher et al. Identification and Optimization of the First Highly Selective GLUT1 Inhibitor BAY-876, ChemMedChem, 2016, 11, 2261-2271.
Stone et al. Mitochondrial metabolism: a target in AR-driven disease, Nature Reviews, Urology vol. 16, p. 1 (2019).
Wei et al. Drug repositioning in head and neck squamous cell carcinoma: An integrated pathway analysis based on connectivity map and differential gene expression, Pathology—Research and Practice, 215 (2019) 152378.
Yip et al. Potential use of alexidine dihydrochloride as an apoptosis-promoting anticancer agent, Mol Cancer Ther 2006;5(9), 2006.
American Cancer Society (ACS), Lung Cancer Survival Rates, 2025, available at https://www.cancer.org/cancer/types/lung-cancer/detection-diagnosis-staging/survival-rates.html.
National Cancer Institute (NCI), Drugs Approved for Lung Cancer, 2025, available at https://www.cancer.gov/about-cancer/treatment/drugs/lung.

* cited by examiner

| id | log₂FoldChange | p-value | Pathway |
|---|---|---|---|
| Glut1/Slc2a1 | 0.901996738 | 8.38E-11 | Glycolysis |
| Hk1 | 0.372723975 | 0.00752185 | Glycolysis |
| Eno1 | 0.442920123 | 5.60E-05 | Glycolysis |
| Ldha | -0.406341713 | 0.05824285 | Glycolysis |
| G6pd | 1.615370795 | 3.97E-34 | Oxidative PPP |
| Pgls | 0.126378283 | 0.3064758 | Oxidative PPP |
| Pgd | 0.820039376 | 6.75E-11 | Oxidative PPP |
| Rpia | -0.09059891 | 0.57039866 | Non-oxidative PPP |
| Rpe | -0.203978841 | 0.06666609 | Non-oxidative PPP |
| Gfpt1 | -0.374128233 | 0.00670859 | Hexose biosynthesis pathway |
FIG. 2A
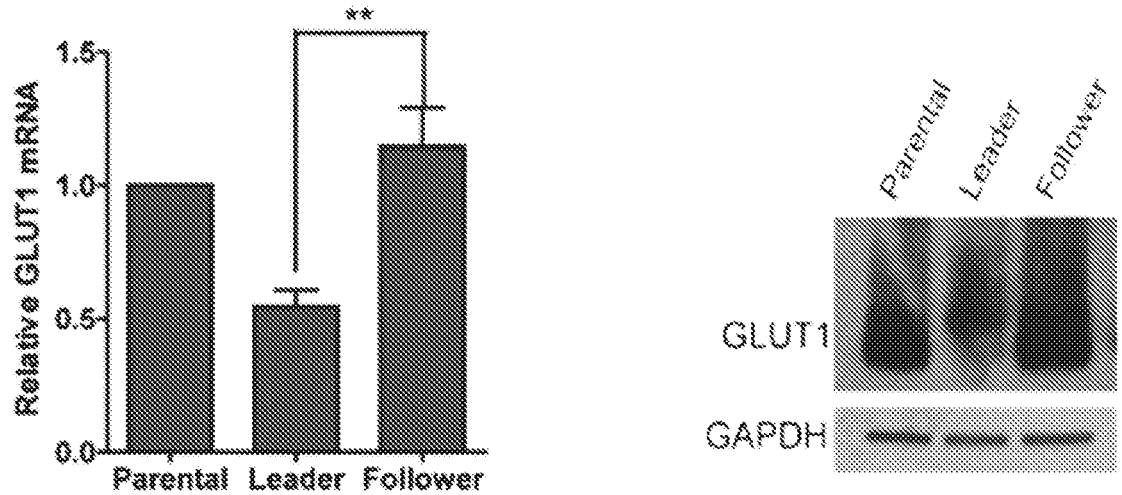
FIG. 2B          FIG. 2C
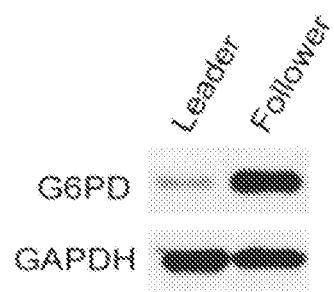
FIG. 2D

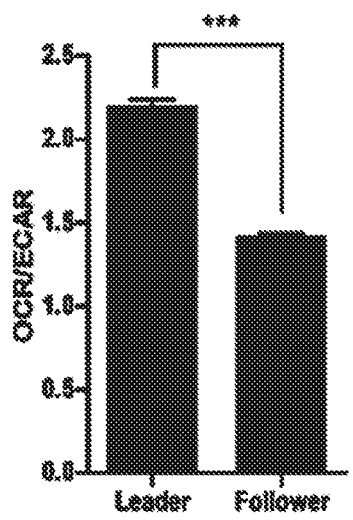
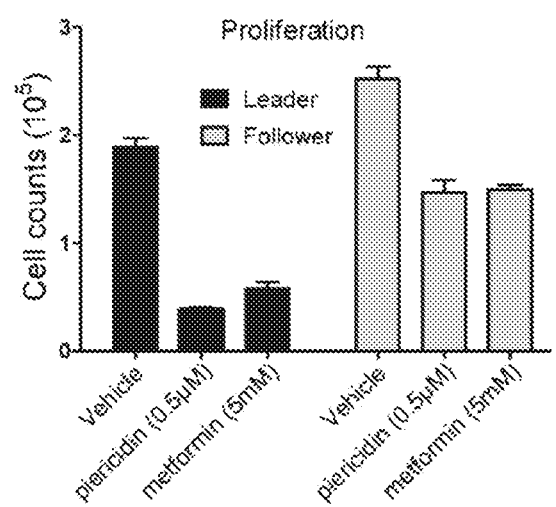
FIG. 3C
FIG. 3D
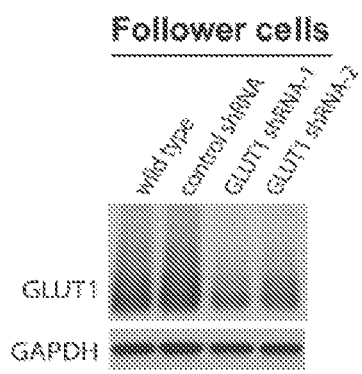
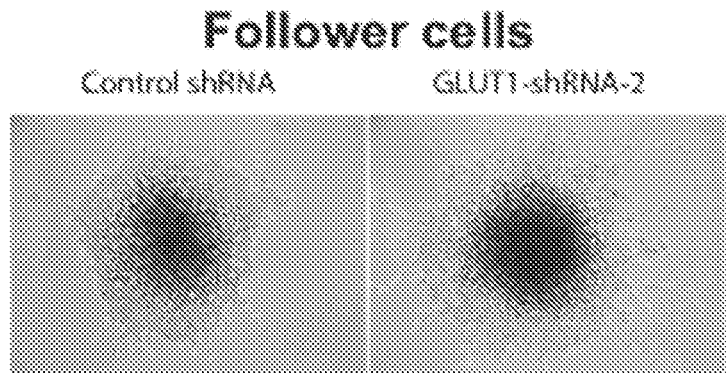
FIG. 4A
FIG. 4B

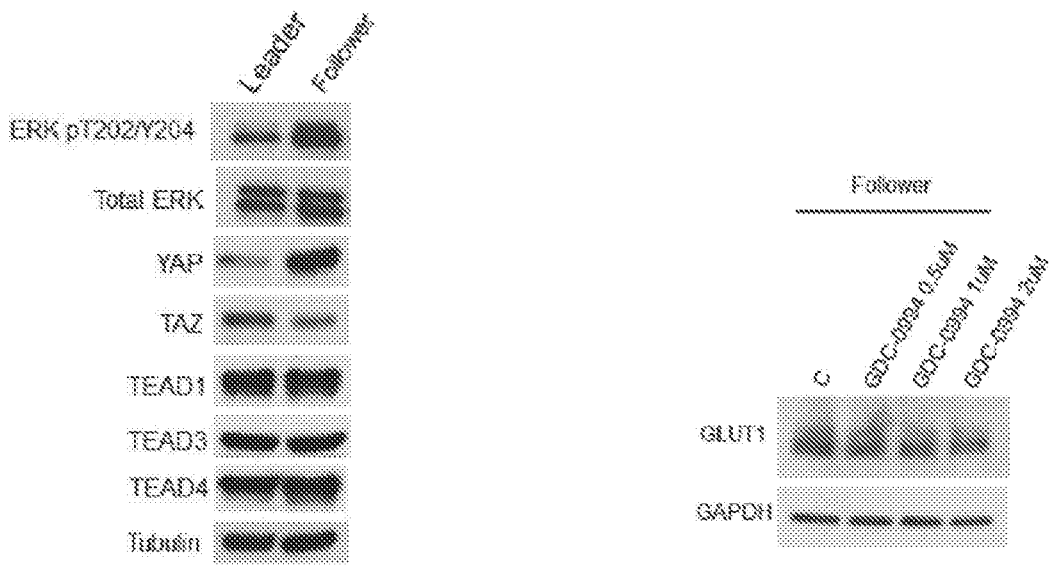
FIG. 7A
FIG. 7B
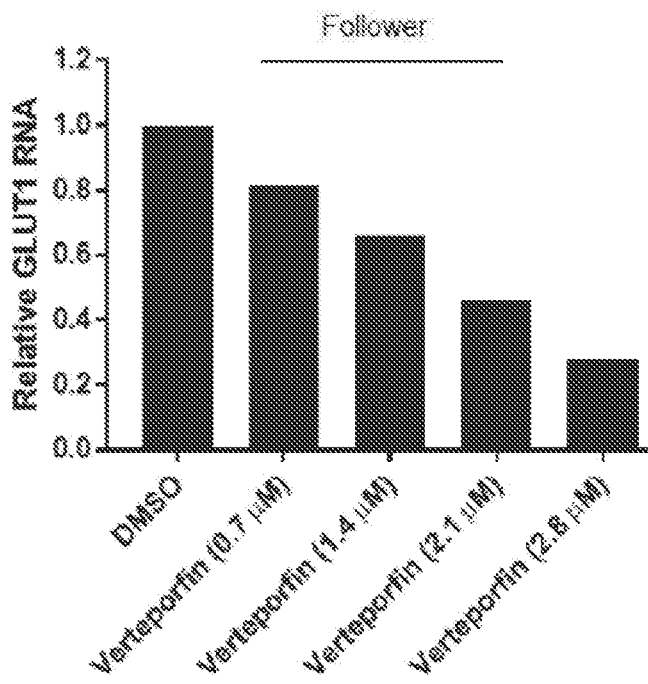
FIG. 7C

COMBINATION THERAPIES FOR MANAGING CANCER

CROSS REFERENCE TO RELATED APPLICATIONS

This application is the National Stage of International Application No. PCT/US2020/041565 filed Jul. 10, 2020, which claims the benefit of U.S. Provisional Application No. 62/872,923 filed Jul. 11, 2019. The entirety of each of these applications is hereby incorporated by reference for all purposes.

BACKGROUND

A single tumor can harbor distinct genetic and epigenetic cellular subpopulations that drive tumor initiation and progression. This intratumor heterogeneity is proposed to be one of the major confounding factors of treatment causing relapse and poor clinical outcome. Genomic instability and epigenetic modifications generate intratumor heterogeneity creating distinct genetic and epigenetic subpopulations or clones. A branched tumor evolutionary architecture can emerge containing the plasticity to progress under harsh environmental conditions and thwart therapeutic attempts to eradicate the tumor. Thus, there is a need to identity improved therapies for treating tumors and related cancers.

Non-small cell lung cancer is an umbrella term for several types of lung cancers that behave in a similar way such as squamous cell carcinoma, adenocarcinoma and large cell carcinoma. Heavy smokers commonly develop small cell lung cancer (SCLC). The outcome for patients with SCLC remains unpredictable. While many SCLC patients respond to frontline chemotherapy, recurrence of disease is common. Recurrence following initial frontline therapy is associated with a higher risk of resistance to the available salvage treatment options. Thus, there is a need to identify improved therapies.

Konen et al. report an image-guided genomics technique termed spatiotemporal genomic and cellular analysis (SaGA) that allows for precise selection and amplification of living and rare cells. Nat Comm, 2017, 8:15078. SaGA was used on collectively invading 3D cancer cell packs to create purified leader and follower cell lines. The leader cell cultures are invasive in contrast to follower cultures that show phenotypic plasticity over time.

Yip et al. report the potential use of alexidine dihydrochloride as an apoptosis-promoting anticancer agent. Mol Cancer Ther, 2006, 5(9):2234-40. See also Graber et al. Oral disinfectants that inhibit protein-protein interactions mediated by the antiapoptotic protein Bcl-xL and induce apoptosis in human oral tumor cells, Angew Chem Int Ed, 2013, 52:4487-4491; Niemi et al. Downregulation of the Mitochondrial Phosphatase PTPMT1 Is Sufficient to Promote Cancer Cell Death, PLoS ONE, 2013, 8(1):e53803; and Lo et al. Computational cell cycle profiling of cancer cells for prioritizing FDA-approved drugs with repurposing potential, Sci Rep, 2017, 7(1):11261.

References cited herein are not an admission of prior art.

SUMMARY

This disclosure relates to methods of managing cancer and tumor growth. In certain embodiments, this disclosure relates to methods of treating cancer comprising administering a combination of chemotherapy agents, wherein a first chemotherapy agent is capable of inhibiting oxidative phosphorylation of pyruvate and a second chemotherapy agent is capable of inhibiting glucose metabolism. In certain embodiments, the first and second chemotherapy agents are administered in combination with an additional chemotherapy agent.

In certain embodiments, the first chemotherapy agent is a pyruvate dehydrogenase (PDH) inhibitor, complex I inhibitor, or a mitochondrial pyruvate carrier inhibitor. In certain embodiments, the first chemotherapy agent is a bis-biguanide compounds, such as alexidine, derivative or salt thereof. In certain embodiments, the first chemotherapy agent is devimistat (6,8-bis(benzylthio)octanoic acid, CPI-613), derivative, or salt thereof. In certain embodiments, the first chemotherapy agent is 2-cyano-3-(1-phenyl-1H-indol-3-yl)-2-propenoic acid (UK 5099), derivative, or salt thereof.

In certain embodiments, the second agent is a glucose transporter 1 inhibitor, yes-associated protein to transcriptional enhanced associate domain inhibitor, glucose-6-phosphate dehydrogenase inhibitor, or extracellular signal-regulated kinase inhibitor. In certain embodiments, the second chemotherapy agent is verteporfin, derivative or salt thereof. In certain embodiments, the second chemotherapy agent is $N^4$-[1-[(4-cyanophenyl)methyl]-5-methyl-3-(trifluoromethyl)-1H-pyrazol-4-yl]-7-fluoro-2,4-quinolinedicarboxamide (BAY-876), derivative or salt thereof. In certain embodiments, the second chemotherapy agent is 6-aminonicotinamide (6AN), dehydroepiandrosterone (DHEA), derivative or salt thereof. In certain embodiments, second chemotherapy agent is ravoxertinib ((S)-1-(1-(4-chloro-3-fluorophenyl)-2-hydroxyethyl)-4-(2-((1-methyl-1H-pyrazol-5-yl) amino) pyrimidin-4-yl) pyridin-2(1H)-one, GDC-0994), derivative or salt thereof.

In certain embodiments, this disclosure contemplates administering a PDH inhibitor such as alexidine or devimistat in combination with a GLUT1 inhibitor, such as BAY-876, optionally in combination with an additional chemotherapy agent.

BRIEF DESCRIPTION OF THE DRAWINGS

FIG. 2A shows data indicating proliferative follower and invasive leader cells exhibit differential GLUT1 and G6PD expression: log 2 fold gene expression changes of proximal glycolytic and PPP pathway genes in follower vs leader cells.

FIG. 2B shows data on GLUT1 mRNA expression in parental, leader and follower cells determined by qRT-PCR.

FIG. 2C shows GLUT1 immunoblot analysis.

FIG. 2D shows G6PD expression in leader and follower cells.

FIG. 3C shows data on OCR/ECAR ratios of follower and leader cells evaluated using a seahorse bioenergetics analyzer.

FIG. 3D shows data indicating an impact of complex I inhibitors on follower/leader proliferation after 72 hrs of treatment that were assessed using trypan blue and an automated cell counter.

FIG. 4A shows data indicating GLUT1 knockdown promotes follower cell invasion. Western blots indicated a stable knockdown of GLUT1 in followers.

FIG. 4B shows spheroids formed with follower cells transfected with control shRNA or GLUT1 shRNA-2 embedded in Matrigel™. Invasive area and circularity of the spheroids were evaluated after 40 hrs.

FIG. 7A shows western blot analysis of pERK, ERK, YAP and TEAD proteins.

FIG. 7B shows GLUT1 expression by western blot where follower cells were treated with indicated doses of ERK inhibitor (GDC-0994) or YAP/TEAD inhibitor (verteporfin) for 24 hrs.

FIG. 7C shows data on GLUT mRNA expression by qRT-PCR.

DETAILED DISCUSSION

Figure 1A:
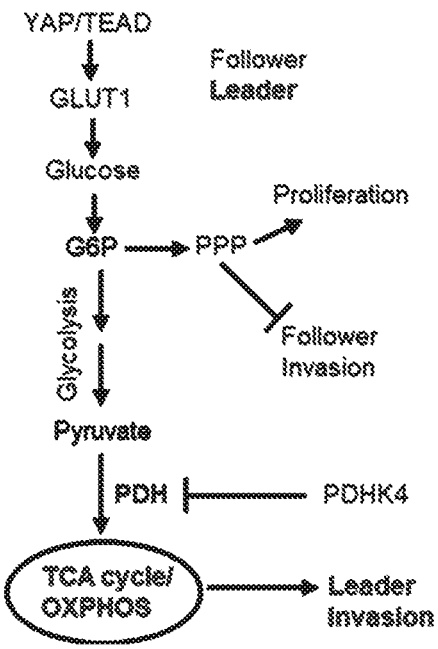
FIG. 1A illustrates an overall model of metabolic heterogeneity among leader and follower cells.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

As used herein, the terms "small cell lung cancer" refers to small cell carcinoma (oat cell cancer) or combined small cell carcinoma identified in lung tissue. Tests and procedures may be used to detect (find), diagnose, and stage small cell lung cancer. A subject may be diagnosed with small cell lung cancer by laboratory tests, sputum cytology, lung biopsy, e.g., fine-needle aspiration (FNA) biopsy of the lung, bronchoscopy, thoracoscopy, thoracentesis, mediastinoscopy, CT scan (CAT scan), or chest x-ray. Test samples of lung tissue or fluid, blood, urine, or other substances in the body may be used. These tests may be used to plan and check treatment or monitor the disease over time.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus. In certain embodiments, contemplated treatments include childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

In certain embodiments, the first and second chemotherapy agent disclosed herein is administered in combination with an additional chemotherapy agent. Another "chemotherapy agent," "chemotherapeutic," "anti-cancer agent" or the like, refer to molecules that are recognized to aid in the treatment of a cancer. Contemplated examples include the following molecules, prodrugs, or derivatives: abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed di sodium, copanli sib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof, such as a combination of cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); and methotrexate, vincristine, doxorubicin, cisplatin (MVAC).

Methods of Use

This disclosure relates to methods of managing cancer and tumor growth. In certain embodiments, this disclosure relates to methods of treating cancer comprising administering a combination of chemotherapy agents, wherein a first chemotherapy agent is capable of inhibiting oxidative phosphorylation of pyruvate and a second chemotherapy agent is capable of inhibiting glucose metabolism. In certain embodiments, the first and second chemotherapy agents are administered in combination with another chemotherapy agent.

In certain embodiments, the first chemotherapy agent is a pyruvate dehydrogenase (PDH) inhibitor, complex I inhibitor, or a mitochondrial pyruvate carrier inhibitor. In certain embodiments, the first chemotherapy agent is a bis-biguanide compounds, such as alexidine or other bis-biguanide compound, derivative, or salt thereof. In certain embodiments, the first chemotherapy agent is devimistat (6,8-bis (benzylthio)octanoic acid, CPI-613), derivative, or salt thereof. In certain embodiments, the first chemotherapy agent is 2-cyano-3-(1-phenyl-1H-indol-3-yl)-2-propenoic acid (UK 5099), derivative, or salt thereof.

In certain embodiments, the second agent is a glucose transporter 1 inhibitor, yes-associated protein to transcriptional enhanced associate domain inhibitor, glucose-6-phosphate dehydrogenase inhibitor, or and extracellular signal-regulated kinase inhibitor. In certain embodiments, the second chemotherapy agent is verteporfin, derivative, or salt thereof. In certain embodiments, the second chemotherapy agent is N4-[1-[(4-cyanophenyl)methyl]-5-methyl-3-(trifluoromethyl)-1H-pyrazol-4-yl]-7-fluoro-2,4-quinolinedicarboxamide (BAY-876), derivative or salt thereof. In certain embodiments, the second chemotherapy agent is 6-aminonicotinamide (6AN), dehydroepiandrosterone (DHEA), derivative or salt thereof. In certain embodiments, second chemotherapy agent is ravoxertinib ((S)-1-(1-(4-chloro-3-fluorophenyl)-2-hydroxyethyl)-4-(2-((1-methyl-1H-pyrazol-5-yl) amino) pyrimidin-4-yl) pyridin-2(1H)-one, GDC-0994), derivative or salt thereof. In certain embodiments, the first and second chemotherapy agents are administered in combination with another chemotherapy agent.

In certain embodiments, this disclosure contemplates PDH inhibitor such as alexidine, or other bis-biguanide compound, or devimistat in combination with a GLUT1 inhibitor, such as BAY-876, optionally in combination with a third chemotherapy agent.

In certain embodiments, this disclosure relates to methods of treating lung cancer comprising administering an effective amount of a combination of agents disclosed herein to a subject in need thereof. In certain embodiments, this disclosure relates to methods of treating small cell lung cancer comprising administering an effective amount of a combination of agents disclosed herein to a subject in need thereof. In certain embodiments, the subject is diagnosed with a lung cancer. In certain embodiments, the subject is diagnosed with small cell lung cancer. In certain embodiments, the subject is a human subject.

In certain embodiments, the disclosure relates to methods of treating or preventing cancer comprising administering a combination of agents disclosed herein to a subject diagnosed with, exhibiting symptoms of, or at risk of cancer. In certain embodiments, the cancer is selected from the group consisting of leukemia, melanoma, cervical, ovarian, colon, breast, gastric, lung, skin, ovarian, pancreatic, prostate, head, neck, and renal cancer. In certain embodiments, the first and second chemotherapy agent disclosed herein is administered in combination with a third chemotherapeutic agent.

In certain embodiments, the disclosure relates to therapeutic methods disclosed herein wherein the first and second chemotherapy agent disclosed herein are administered before, after or during radiotherapy.

In certain embodiments, the subject is a human subject. In certain embodiments, this disclosure contemplates use as a first line treatment and use as a second line treatment, e.g., after growth of small cell lung cancer returns after a period of remission. In certain embodiments, the subject previously received a first chemotherapy treatment such as an administration schedule of etoposide, cisplatin, carboplatin, irinotecan, or combinations thereof.

In certain embodiments, this disclosure relates to methods of treating small cell lung cancer comprising administering an effective amount of a first and second chemotherapy agent disclosed herein in combination with cisplatin to a subject in need thereof.

In certain embodiments, this disclosure relates to methods of treating small cell lung cancer comprising administering an effective amount of a first and second chemotherapy agent disclosed herein in combination with etoposide to a subject in need thereof.

In certain embodiments, this disclosure relates to methods of treating small cell lung cancer comprising administering an effective amount of a first and second chemotherapy agent disclosed herein in combination with irinotecan to a subject in need thereof.

In certain embodiments, this disclosure relates to methods of treating small cell lung cancer comprising administering an effective amount of a first and second chemotherapy agent disclosed herein in combination with carboplatin, to a subject in need thereof.

In certain embodiments, this disclosure relates to methods of treating small cell lung cancer comprising administering an effective amount of a first and second chemotherapy agent disclosed herein in combination with cisplatin and etoposide to a subject in need thereof.

In certain embodiments, this disclosure relates to methods of treating small cell lung cancer comprising administering an effective amount of a first and second chemotherapy agent disclosed herein in combination with carboplatin and etoposide to a subject in need thereof.

In certain embodiments, this disclosure relates to methods of treating small cell lung cancer comprising administering an effective amount of a first and second chemotherapy agent disclosed herein in combination with carboplatin and irinotecan to a subject in need thereof.

In certain embodiments, methods contemplate administration in cycles with a period of treatment of daily for 1 to 3 days followed by a rest period of at least one, two, three or more days. In certain embodiments, the cycle generally lasts about 2 to 4 weeks, and/or for 2 to 6 cycles, 2 to 7 cycles, or 2 to 8 cycles.

In certain embodiments, this disclosure contemplates methods wherein if during initial treatment cancer progresses during treatment or returns after treatment with etoposide, cisplatin, irinotecan, or combinations thereof, then the subject is administered a cycle of a first and second chemotherapy agent disclosed herein optionally in combination with other chemotherapy agents.

As used herein, a "pyruvate dehydrogenase (PDH) inhibitor," is any molecule, steroid, peptide, antibody, or nucleic acid that specifically binds to pyruvate dehydrogenase and reduces the rate at which PDH breaks down pyruvate. Examples include devimistat (6,8-bis(benzylthio)octanoic acid, CPI-613), 4-(4-(4-methoxyphenyl)-5-methyl-1H-pyrazol-3-yl)benzene-1,3-diol (M77976), N-oxalylglycine, R-lipoic acid, dichloroacetate, 2-chloroprorionate, 4-(2,5-dimethyl-4-(4,4,4-trifluoro-3-hydroxy-3-methylbut-1-en-2-yl)piperazine-1-carbonyl)benzonitrile (Nov3 r), 4-[3-chloro-4-[[(2R)-3,3,3-trifluoro-2-hydroxy-2-methyl propanoyl]amino]phenyl]sulfonyl-N,N-dimethylbenzamide (AZD7545), N-(2-aminoethyl)-2-{3-chloro-4-[(4-isopropylbenzyl)oxy] phenyl} acetamide, monorden, mitaplatin, phenylbutyrate, and honokiol dichloroacetate ester, derivatives or salts thereof.

As used herein, a "complex I inhibitor," refers to any molecule, steroid, peptide, antibody, or nucleic acid that specifically binds to an NADH:ubiquinone oxidoreductase complex of the mitochondrial electron transport chain and reduces the rate at which NADH is oxidized. Examples include metformin, phenformin, cycloguanil, proguanil, galegine, amiloride, 5-(N-ethyl-N-isopropyl)amiloride (EIPA), 5-(N-methyl-N-isobutyl)amiloride (MIA), benzamil, 1-methyl-4-phenyl-1,2,3,6-tetrahydropyridine (MPTP), clozapine, haloperidol, chlorpromazine, thiothixene, rotenone and piericidin A, derivatives or salts thereof.

As used herein, a "mitochondrial pyruvate carrier inhibitor" refers to any molecule, steroid, peptide, antibody, or nucleic acid that binds to a mitochondrial pyruvate carrier (MPC) complex, MPC comprises two proteins, MPC1 and MPC2, in the inner mitochondrial membrane and suppress transport of pyruvate into the mitochondrial matrix. Examples include (E)-2-Cyano-3-(1-phenyl-1H-indol-3-yl) acrylic acid (UK5099), 7-(benzyl(methyl)amino)-2-oxo-2H-chromene-3-carboxylic acid (7ACC2), pioglitazone, rosiglitazone, lobeglitazone, tolylfluanid, and tributyltin, derivatives or salts thereof.

As used herein, a "glucose transporter 1 inhibitor," refers to any molecule, steroid, peptide, antibody, or nucleic acid that binds to glucose transporter 1 and reduces the transport of glucose across plasma membranes. Examples include alexidine, bis-biguanide compounds, fasentin, 3-fluoro-1,2-phenylene bis(3-hydroxybenzoate) (WZB 117), 4-[[[[4-(1, 1-dimethylethyl) phenyl] sulfonyl]amino]methyl]-N-3-pyridinylbenzamide (STF31), and N4-[1-(4-cyanobenzyl)-5-methyl-3-(trifluoromethyl)-1H-pyrazol-4-yl]-7-fluoroquinoline-2,4-dicarboxamide (BAY-876), derivatives or salts thereof.

As used herein a "bis-biguanide compound" refers to a compound with two bridging biguanidine groups, i.e., (—NH(C=NH)NH(C=NH)NH—), connected by a linking group. In certain embodiments, a bis-biguanide compound is alexidine [1,1'-(hexane-1,6-diyl)bis(5-(2-ethylhexyl)biguanidine)] and derivatives and chlorhexidine [1,1'-(hexane-1, 6-diyl)bis(3-(4-chlorophenyl)biguanidine)] and derivatives salts thereof, including the digluconate and the diacetate salts, especially the digluconate salts. Other salts include the dipropionate, the diformate, the dilactate, the dihydrochloride, the dihydrofluoride, the dihydrobromide, the sulfate, the phosphate, the succinate, the pivalate, the citrate, the tartrate and the maleate. In certain embodiments, the bis-biguanide compound is chlorhexidine. In certain embodiments, the bis-biguanide or alexidine derivative has Formula I:

Formula I

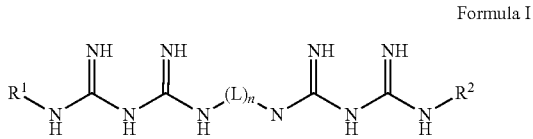

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents.

In certain embodiments, L is at each occurrence individually and independently selected from O, NH, C=O, $CH_2$, $OCH_2$, $CH_2O$, $NHCH_2$, $CH_2NH$, $OCH_2CH_2$, $CH_2CH_2O$, $NHCH_2CH_2$, or $CH_2CH_2NH$.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched alkyl optionally substituted with one or more substituents and n is 2 to 8. In certain embodiments, $R^1$ is a branched alkyl optionally substituted with one or more substituents and n is 2 to 12. In certain embodiments, $R^1$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched alkyl optionally substituted with one or more substituents and n is 2 to 8. In certain embodiments, $R^2$ is a branched alkyl optionally substituted with one or more substituents and n is 2 to 12. In certain embodiments, $R^2$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched phenyl optionally substituted with one or more substituents and n is 2 to 8. In certain embodiments, $R^1$ is a branched phenyl optionally substituted with one or more substituents and n is 2 to 12. In certain embodiments, $R^1$ is a branched phenyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched phenyl optionally substituted with one or more substituents and n is 2 to 8. In certain embodiments, $R^2$ is a branched phenyl optionally substituted with one or more substituents and n is 2 to 12. In certain embodiments, $R^2$ is a branched phenyl optionally substituted with one or more substituents and n is 2 to 22.

Alexidine has the chemical name 1,1'-(hexane-1,6-diyl)bis(5-(2-ethylhexyl)biguanidine). Additional contemplated alexidine derivatives include: 1-(2-ethylhexyl)-5-propyl-biguanidine (AX-1), 1,1'-(hexane-1,6-diyl)bis(5-(2-ethylhexyl)biguanidine) (AX-2), 1,1'-(butane-1,4-diyl)bis(5-(2-ethylhexyl)biguanidine) (AX-3), 1,1'-(octane-1,8-diyl)bis(5-(2-ethylhexyl)biguanidine) (AX-4), 1,1'-(hexane-1,6-diyl)bis(5-(2-butylhexyl)biguanidine) (TG-AX5), 1,1'-(hexane-1,6-diyl)bis(5-(2-ethylbutyl)biguanidine) (TG-AX7), 1,1'-(hexane-1,6-diyl)bi(5-(4-methoxybutyl)biguanidine) (TG-AX10).

As used herein, a "yes-associated protein to transcriptional enhanced associate domain inhibitor" refers to any molecule, steroid, peptide, antibody, or nucleic acid that binds to YAP (Yes1-associated protein), TAZ (transcriptional co-activator with PDZ-binding motif), or TEAD (transcriptional enhanced associate domain) and impairs the function of TEAD to increase expressions of such target gene such as CTGF (connective tissue growth factor), CYR61 (cysteine-rich angiogenic inducer 61), AXL (AXL receptor tyrosine kinase), or BIRC5 (baculoviral inhibitor of apoptosis repeat-containing 5 or survivin). Examples include digitoxin, verteporfin, flufenamic, dasatinib, dobutamine, dimethyl fumarate, erlotinib, fluvastatin, gefitinib, pazopanib, losmapimod, melatonin, trametinib, derivatives or salts thereof.

As used herein, a "glucose-6-phosphate dehydrogenase inhibitor," refers to any molecule, steroid, peptide, antibody, or nucleic acid that binds to glucose-6-phosphate dehydrogenase and reduces the production of NADPH. Examples include dehydroepiandrosterone (DHEA), 6-aminonicotinamide (ANAD), dantrolene, 3,4',5-trihydroxystilbene-3-β-d-glucoside; trans-resveratrol 3-β-mono-D-glucoside (polydatin, piceid), derivatives or salts thereof.

As used herein, a "extracellular signal-regulated kinase inhibitor," refers to any molecule, steroid, peptide, antibody, or nucleic acid that binds to extracellular signal-regulated kinase in a cell and reduces the proliferation of the cell. Examples include ravoxertinib (GDC-0994), (R)-1-(2-oxo-2-(4-(4-(pyrimidin-2-yl)phenyl)piperazin-1-yl)ethyl)-N-(3-(pyridin-4-yl)-1H-indazol-5-yl)pyrrolidine-3-carboxamide (SCH772984), (R)-7-(3,4-difluorobenzyl)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one (AZD0364), (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide (MK-8353), (3S,3aR,6S,6aR)-3-(3,4-dimethoxyphenyl)-6-(3,4,5-trimethoxyphenyl)-1,3,3a,4,6,6a-hexahydrofuro[3,4-c]furan (magnolin), 6,6-dimethyl-2-(2-((1-methyl-1H-pyrazol-5-yl)amino)pyrimidin-4-yl)-5-(2-morpholinoethyl)-5,6-dihydro-4H-thieno[2,3-c]pyrrol-4-one (LY3214996), 4-[2-(2-chloro-4-fluoroanilino)-5-methylpyrimidin-4-yl]-N-[(1S)-1-(3-chlorophenyl)-2-hydroxyethyl]-1H-pyrrole-2-carboxamide (VX-11e), derivatives and salts thereof.

As used herein, the term "derivative" refers to a structurally similar compound that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more compounds linked together by a linking group. It is contemplated that the linking group may be biodegradable. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, a "lipid" group refers to a hydrophobic group that is naturally or non-naturally occurring that is highly insoluble in water. As used herein, a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, 2nd Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —C(OH)$R_m$, —C(OH)(OH)—, —C(OH)H, —C(Hal)$R_m$—, —C(Hal)(Hal)-, —C(Hal)H—, —C($N_3$)$R_m$—, —C(CN)$R_m$—, —C(CN)(CN)—, —C(CN)H—, —C($N_3$)($N_3$)—, —C($N_3$)H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100 or 50 or 25 or 10. Examples of linking groups include bridging alkyl groups and alkoxyalkyl groups.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

EXAMPLES

Co-Targeting Metabolic Heterogeneity for Lung Cancer Metastasis/Collective Cell Invasion Metastatic disease is the primary cause of cancer patient death, underscoring the need to identify actionable targets regulating cell invasion. It is not a single metastatic cell but rather collective packs of invasive cells that are observed histologically. The lung cancer tumors are comprised of hierarchical groups of invasive leader and proliferative follower cells which invade surrounding areas as a cohesive unit during metastasis.

Using RNASeq, CE-MS metabolite profiling, cellular energetics and metabolite uptake assays, experimental data indicates that followers consume twice as much glucose as leaders, as well as rely on glycolysis and the oxidative pentose phosphate pathway (PPP) to maintain proliferation and prevent invasion. By disrupting the glucose transporter, GLUT1 followers take on a more leader-like invasive phenotype. Our preliminary data suggest that GLUT1 expression is maintained via a YAP/TEAD transcriptional axis active in followers only. In contrast, using pharmacological and genetic perturbation of PDH, experimental data indicates that leaders rely on oxidative phosphorylation (OXPHOS) via pyruvate dehydrogenase (PDH) activity to drive invasion. PDH activation serves as a node for leader invasion, and preliminary data suggest that PDHK4 (PDH kinase repressor) promoter hypermethylation in leaders contributes to increased PDH activity (FIG. 1A).

Figure 1B:
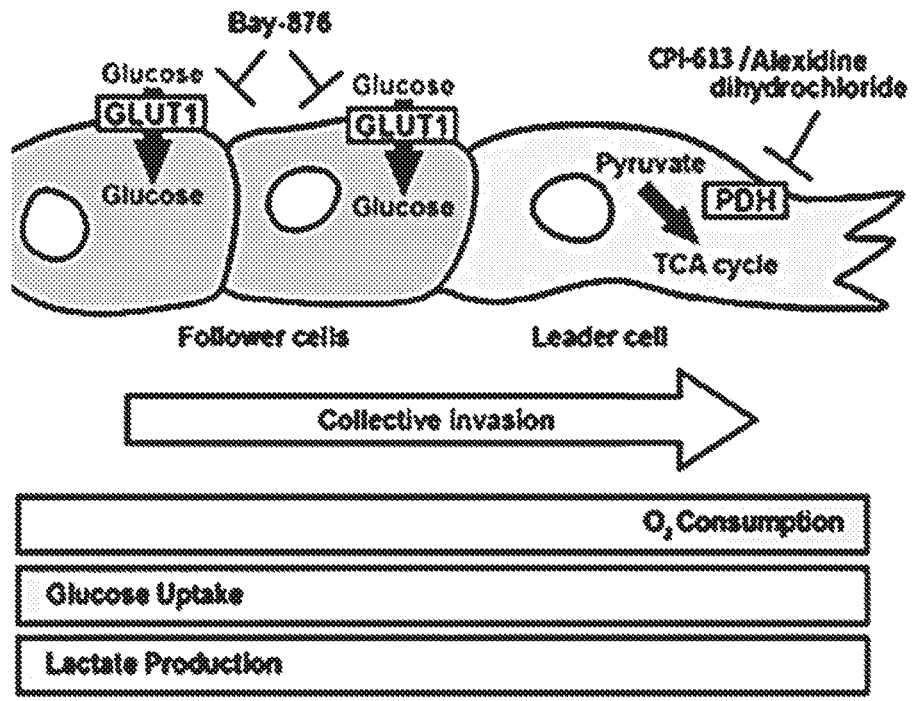
FIG. 1B illustrates a therapeutic strategy to co-target both populations.

Although it is not intended that this disclosure be limited by any particular mechanism, it is believed that metabolic heterogeneity sustained by differential GLUT1 and PDH activity facilitates lung cancer metastasis by maintaining distinct phenotypes in the collective invasion pack. Metabolic heterogeneity fosters a cooperative biology and consequently warrants a co-targeting therapeutic approach to inhibit metastasis. Thus, experiments were performed to determine if co-targeting different metabolic subpopulations limits metastasis (FIG. 1B).

GLUT1 and G6PD are Differentially Expressed in Follower Vs Leader Cells

Figure 2E:
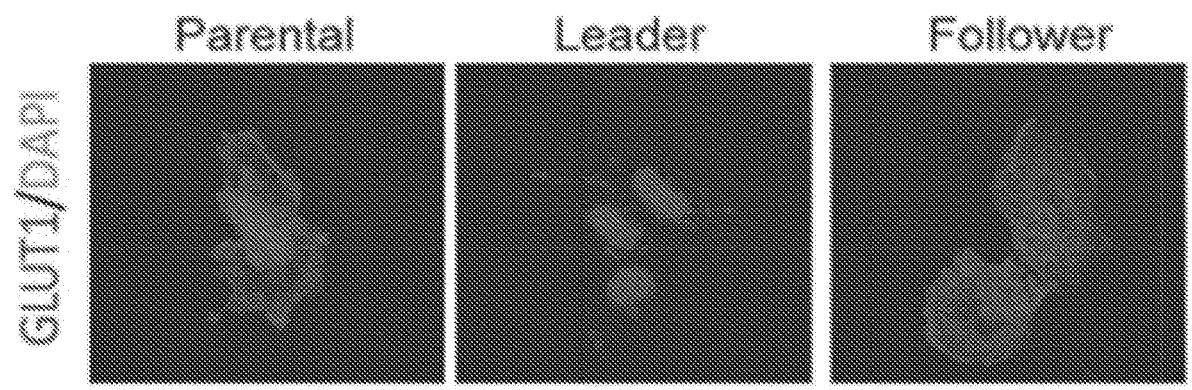
FIG. 2E shows immunofluorescence staining of GLUT1.

RNAseq was performed on purified leader and follower cells with subsequent analysis of glycolysis and PPP-related metabolic genes (FIG. 2A). Among the glycolysis, oxidative and non-oxidative PPP related genes, elevated GLUT1 and G6PD expression was detect in follower cells. Differential GLUT1 expression was validated by qRT-PCR, protein expression, and cellular fluorescence (FIGS. 2B, 2C, 2E). GLUT1 is a high affinity glucose transporter and proximal rate-limiting step in glucose metabolism. GLUT family members are frequently implicated in cancers linked to poor survival and prognosis. Follower cells also have elevated expression of G6PD (FIG. 2D), which catalyzes the first rate-limiting step in the oxidative arm of the PPP and suggests elevated oxidative PPP activity in this cell type.

Figure 3A:
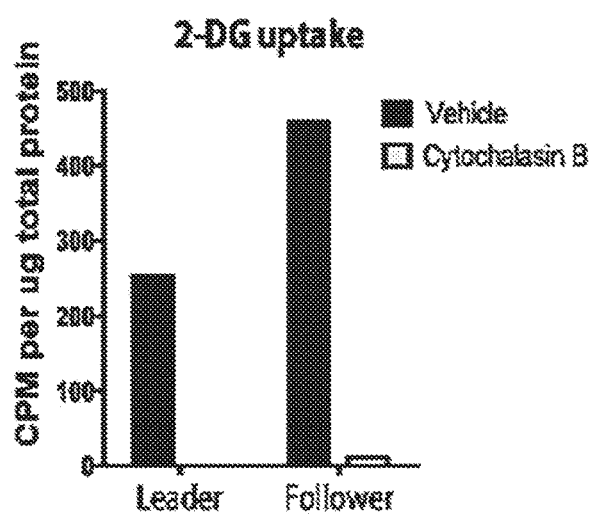
FIG. 3A shows data indicating leader and follower cells exhibit differential glucose uptake, metabolism, PDH phosphorylation and PDHK4 expression. Glucose uptake of leader and follower cells were evaluated in a 6-minute 2-[3H]-deoxyglucose uptake assay. Cytochalasin B (20 µM) was used to inhibit all glucose transport and determine non-specific glucose entry.
Figure 3B:
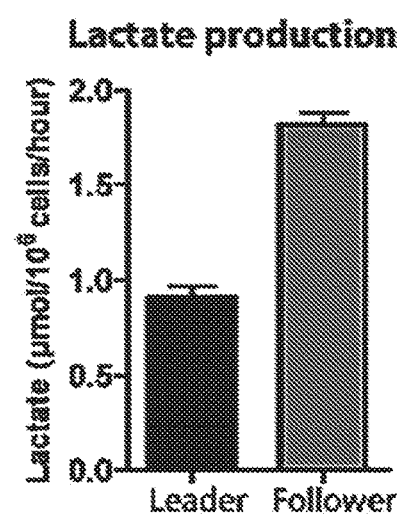
FIG. 3B shows data on extracellular lactate levels in leader and follower culture media (after 6 hours culture) that were estimated using a lactate oxidase colorimetric assay kit.

Follower Cells Exhibit Elevated Glucose Uptake, Glycolysis and Oxidative PPP Activity Experiments were performed to determine whether differential GLUT1 and G6PD expression foster differential metabolism. Data indicates that follower cells consume twice as much glucose and produce more lactate, i.e. supporting elevated glycolysis (FIGS. 3A and 3B). To assess the relative dependence on OXPHOS vs glycolysis, basal oxygen consumption rate (OCR)/extracellular acidification rate (ECAR) ratios were evaluated. Leaders exhibit a significantly higher OCR/ECAR ratio (FIG. 3C), increased coupled OCR (not shown), and increased sensitivity to piericidin and metformin (complex I inhibitors) (FIG. 3D). This indicates increased dependence on OXPHOS. Capillary electrophoresis-mass spectrometry (CE-MS)-targeted comparative metabolite profiling was performed to investigate metabolic pathway reliance. An increase in key glycolytic intermediates was detect in followers, including F6P, F1,6P, DHAP, DPG, 3PG, 2PG, PEP, pyruvate, and lactate, consistent with increased glycolysis in followers. Elevated ribose-5-phosphate (R5P) levels, a key PPP intermediate and precursor of ribonucleotides, lower glucose-6-phosphate (G6P) to R5P ratio and elevated 6PG and PRPP levels was observed suggesting upregulated oxidative PPP activity in follower cells. Taken together, these results indicate elevated glucose uptake, glycolysis and oxidative PPP activity in followers, in contrast to elevated OXPHOS in leaders.

GLUT1 and G6PD are Drivers of the Follower Cell Phenotype

Figure 4C:
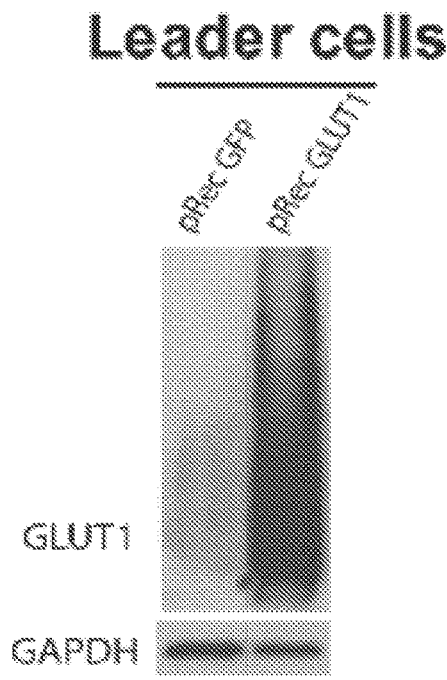
FIG. 4C shows data on immunoblots of leaders demonstrating overexpression of GLUT1.
Figure 4D:
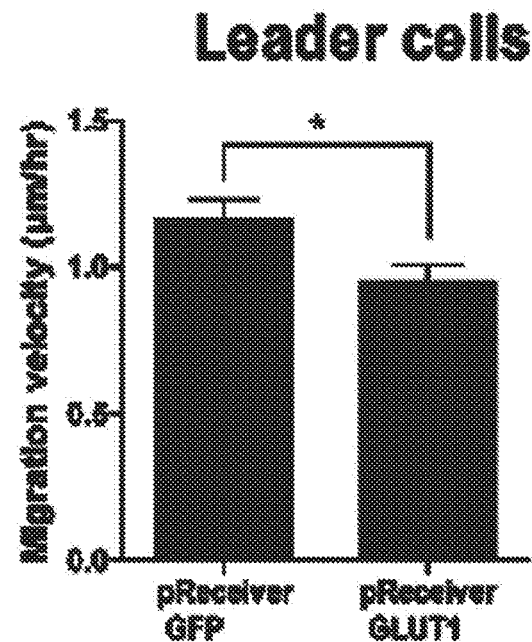
FIG. 4D shows data on the migration of leaders overexpressing GLUT1.
Figure 4E:
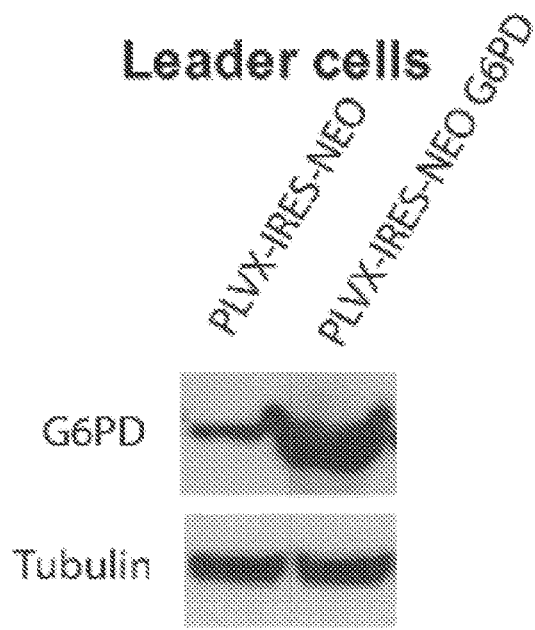
FIG. 4E shows data on immunoblots of G6PD expression in leaders transfected with control or G6PD expression vectors.
Figure 4F:
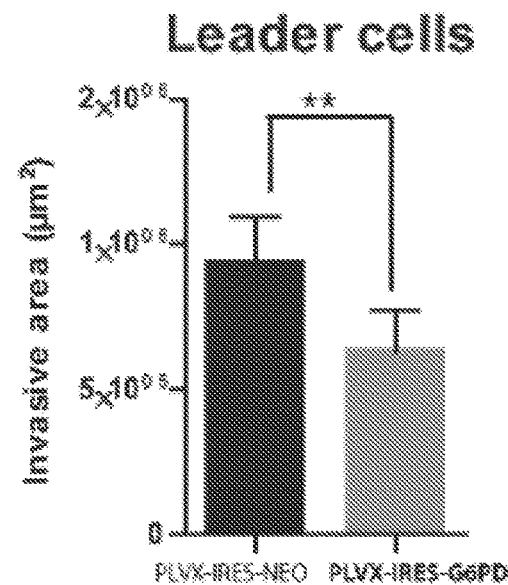
FIG. 4F shows data on invasive areas evaluated after 40 hrs. Spheroids formed with leader cells from (FIG. 4E) were mixed with followers embedded in Matrigel™.

To interrogate the functional significance of elevated GLUT1 expression in followers, knocked down (KD) assays of GLUT1 were performed (FIG. 4A). GLUT1 KD follower cells have increased 3-D invasion and decreased circularity (FIG. 4B), and decreased proliferation, thereby shifting to a more leader-like phenotype. Conversely, GLUT1 overexpression in leaders (FIG. 4C) suppresses motility creating a more follower-like phenotype (FIG. 4D), and increased proliferation. Similarly, G6PD overexpression in leader cells suppresses leader cell invasion (FIGS. 4E and 4F), further supporting that the GLUT1-G6PD pathway is important for suppressing invasion and creating a follower-like biology.

PDH Activation Drives an Invasive Leader Phenotype

Figure 5A:
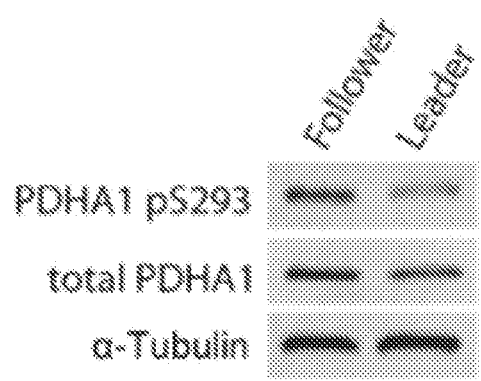
FIG. 5A shows data indicating PDH modulation drives invasive phenotype switching: Western blot of pPDHA1 and total PDHA1 showing increased activity in leaders (decreased phosphorylation) P.
Figure 5B:
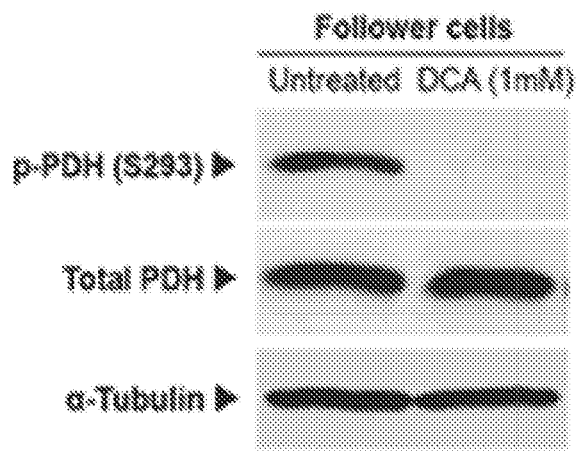
FIG. 5B shows western blot of p-PDHS293, confirming efficacy of DCA treatment after 24 hr.
Figure 5C:
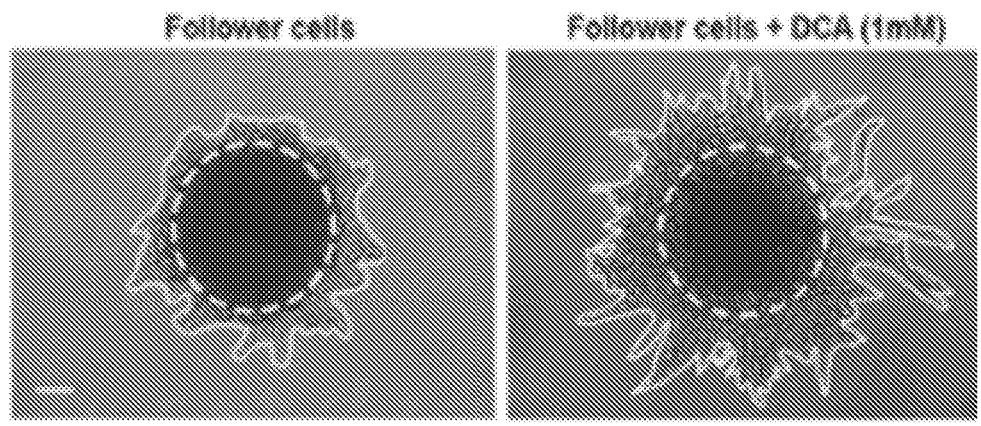
FIG. 5C shows spheroid invasion assays showing increased invasion in followers after DCA treatment. Scale bar=50 μm.
Figure 5D:
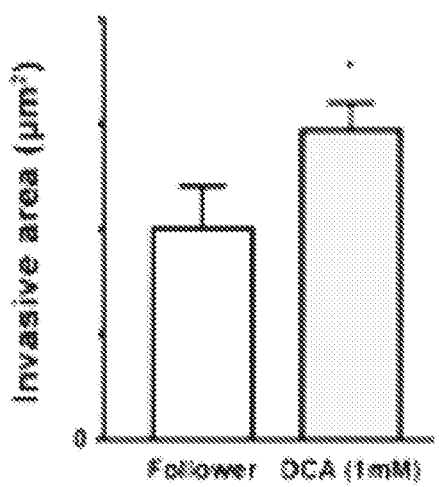
FIG. 5D shows a bar graph of data in FIG. 5C.
Figure 5E:
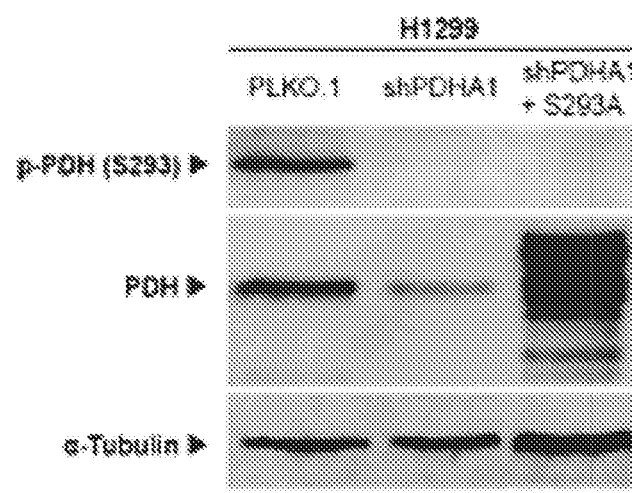
FIG. 5E shows data where H1299 stable cell lines were generated with empty PLKO.1, shPDHA1, and PDH S293A.
Figure 5F:
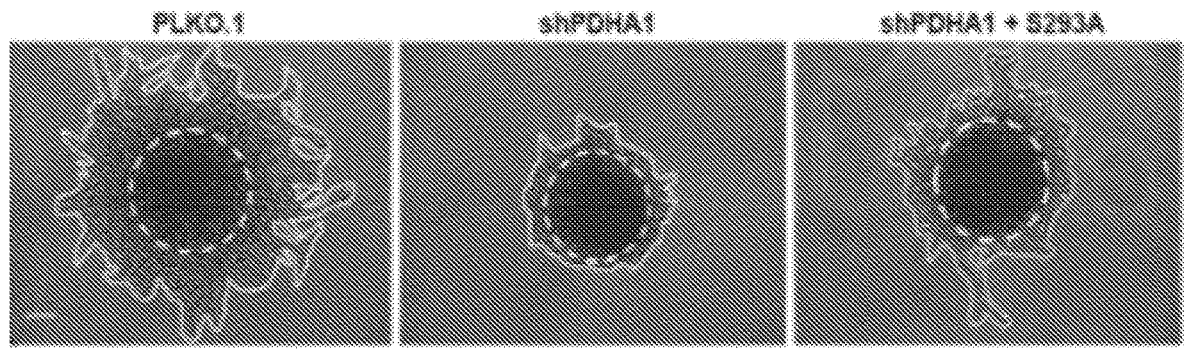
FIG. 5F shows cell lines in FIG. 5E were embedded as spheroids where PDHA1 depletion suppressed invasion but this is partially rescued with the S293A mutant.
Figure 5G:
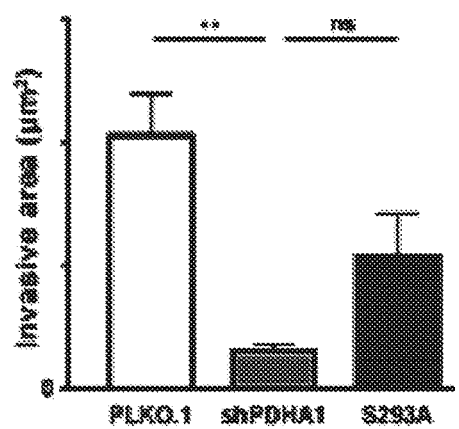
FIG. 5G shows data quantifying the invasive area from FIG. 5F.

To examine the basis for elevated OXPHOS in leaders, pyruvate dehydrogenase (PDH) activation state was evaluated. PDH decarboxylates pyruvate to acetyl-CoA and plays a gate-keeper role linking glycolysis to the tricarboxylic acid (TCA) cycle and OXPHOS. PDH E-1alpha phosphorylation was assessed, which inversely correlates with PDH activity. Follower cells showed higher inactivating p-PDHS293 supporting reduced glucose contribution to TCA cycle activity and OXPHOS. In contrast, leader cells had lower p-PDHS293 (FIG. 5A). To further define the role of PDH, cells were treated with the PDHK inhibitor dichloroacetate (DCA), which decreased p-PDHS293 (FIG. 5B). Followers treated with DCA, transition to a more leader-like phenotype with increased chain-like invasion (FIGS. 5C and 5D). PDH was depleted via PDHA1 targeted shRNA (FIG. 5E). This led to decreased collective invasion that could be partially rescued with a constitutively active PDHS293A (FIGS. 5F and 5G). Taken together, these data indicate that PDH is a key node within the leader metabolism.

PDHK4 is Elevated in Leader Cells vs Follower Cells

Figure 6A:
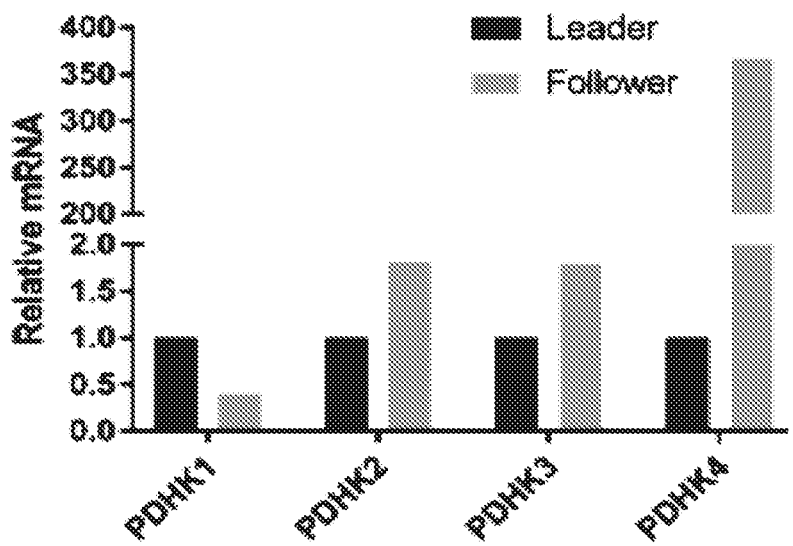
FIG. 6A shows data on mRNA expression of PDHK isoforms by qRT-PCR.
Figure 6B:
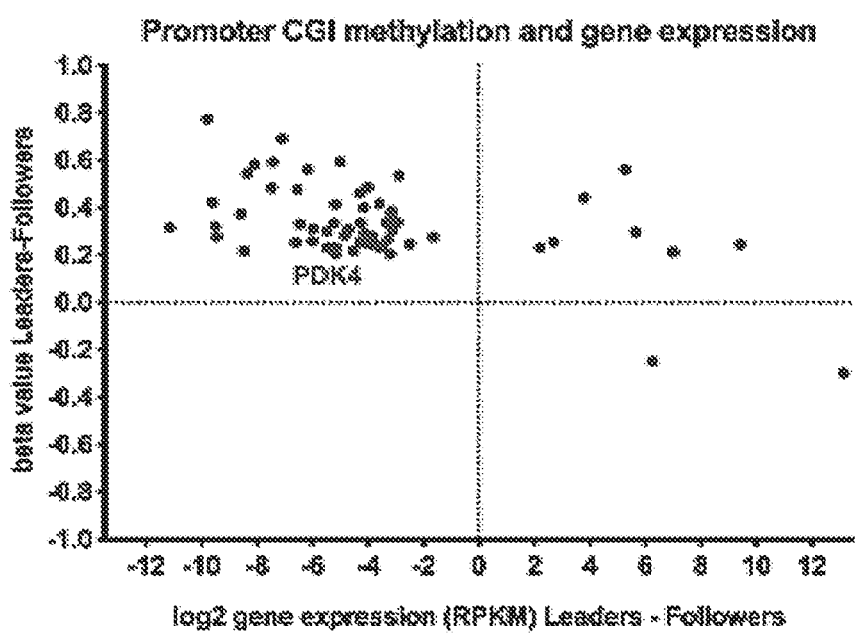
FIG. 6B shows data indicating a high percentage of PDHK4 promoter methylation in leaders. Pdk4 promoter hypermethylation in leaders correlates with decreased mRNA expression. Scatter plot demonstrates promoter methylation and gene expression difference between leaders and followers.

PDH regulates oxidative decarboxylation of pyruvate, linking glucose oxidation with the TCA cycle and oxidative phosphorylation in the mitochondria. PDH activity is suppressed by phosphorylation on serine 293 in the PDHE1A subunit. Preliminary data indicates increased pSer293-PDH in followers (FIG. 5A), and PDH activation upon DCA treatment, or using a constitutively active PDH construct (S293A), promotes invasion. PDH is phosphorylated and inactivated by pyruvate dehydrogenase kinase isoforms 1-4 (PDHK1-4). To probe how PDH is regulated in collective invasion, expression of all four PDHK isoforms were evaluated. RNASeq and qRT-PCR (FIG. 6A) indicate that PDHK4 expression is significantly elevated in followers vs. leaders. Consistent with this finding, interrogation of the follower/leader methylome identified PDHK4 as one of the top differentially methylated genes, where PDHK4 is the only PDHK family member hypermethylated in leaders (FIG. 6B). These data suggest that PDHK4 could be the upstream kinase regulating PDH during collective invasion.

Figure 7D:
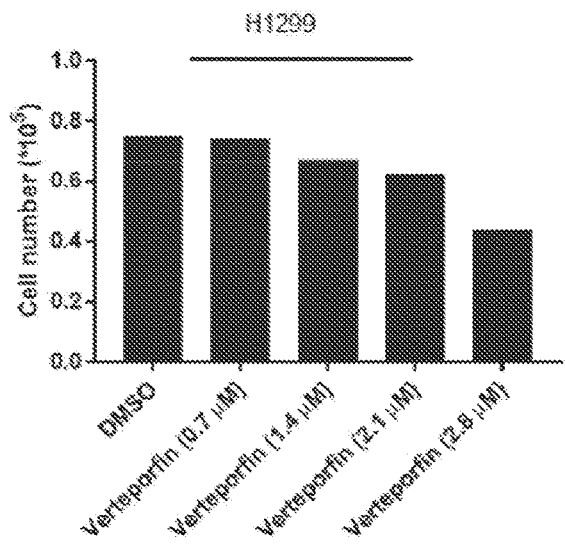
FIG. 7D shows cell number data where H1299 cells were treated with verteporfin for 72 hours and were evaluated for viability.
Figure 7E:
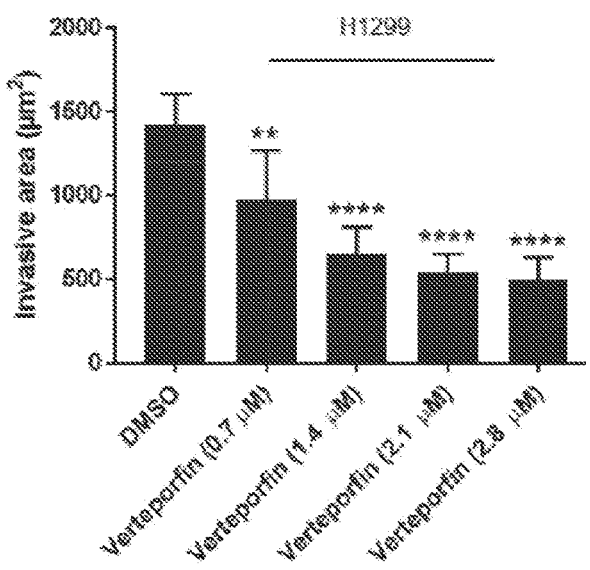
FIG. 7E shows invasive area data from spheroid invasion assays.
Figure 7F:
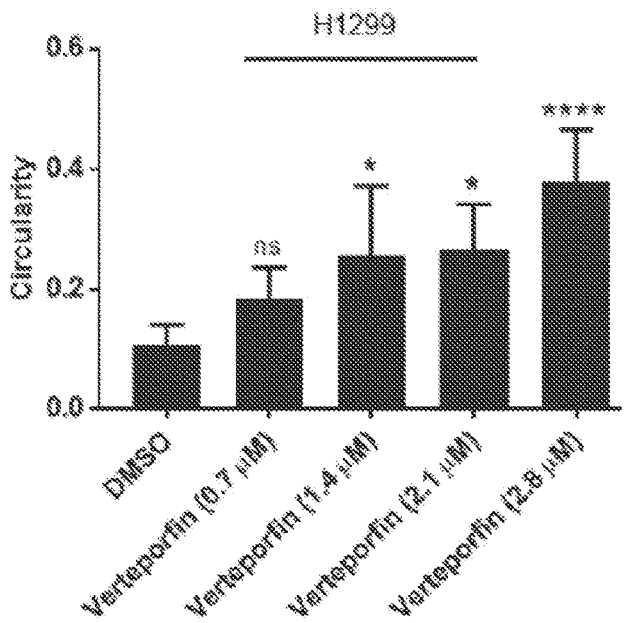
FIG. 7F shows circularity data.

Hippo YAP/TEAD Signaling Pathway is Activated in Leaders and Potentially Responsible in Inducing GLUT1 Expression to Sustain Glycolysis and PPP Activity in Proliferating Followers To determine how GLUT1 expression in followers could be regulated upstream, signaling alterations that might contribute to altered GLUT1 expression in leaders and followers were evaluated. YAP and TAZ are transcriptional co-activators of TEAD (Hippo signaling) and regulate GLUT1 expression. YAP/TEAD 1-4 members were interrogated. Elevated YAP expression was observed in followers (FIG. 7A), suggesting differential regulation between cell types. Cells were treated with the YAP/TEAD inhibitor, verteporfin, which has promising anti-tumor activity. Verteporfin suppressed GLUT1 mRNA expression in followers in a dose-dependent manner (FIG. 7C). Importantly, inhibition of YAP/TEAD also significantly reduced the proliferative and invasive properties of parental H1299 cells (FIGS. 7D and 7E), supporting the concept that YAP/TEAD/GLUT1 are drivers of collective invasion. This data indicates that the Hippo signaling pathway effectors YAP/TEAD transcriptionally regulate GLUT1 expression in followers.

Alexidine Dihydrochloride Induces Metabolic Reprogramming of Leader Cells Via S293 Phosphorylation of PDH Leader cells are resistant to most common chemotherapeutic agents when compared to follower cells suggesting that leader cells cannot be targeted using standard therapeutics. Compounds were screened, and it was discovered that most compounds effective at inhibiting lead cells were typically anti-metabolic agents that disrupt OXPHOS. One such compound, alexidine hydrochloride targets mitochondrial function. Leader cells are sensitive to mitochondria-targeting agents as a class. Alexidine treatment results in a dose-dependent inhibition of collective invasion across multiple lung cell lines. This decrease in invasiveness occurs at doses lower than those that induce cell death, and at earlier time points prior to the effect on cell proliferation suggesting that the anti-invasive activity of alexidine is not due to a proliferation inhibition. This is further supported by data showing that even after 72 hours, there is no significant amount of cell death in leader cells.

Figure 8A:
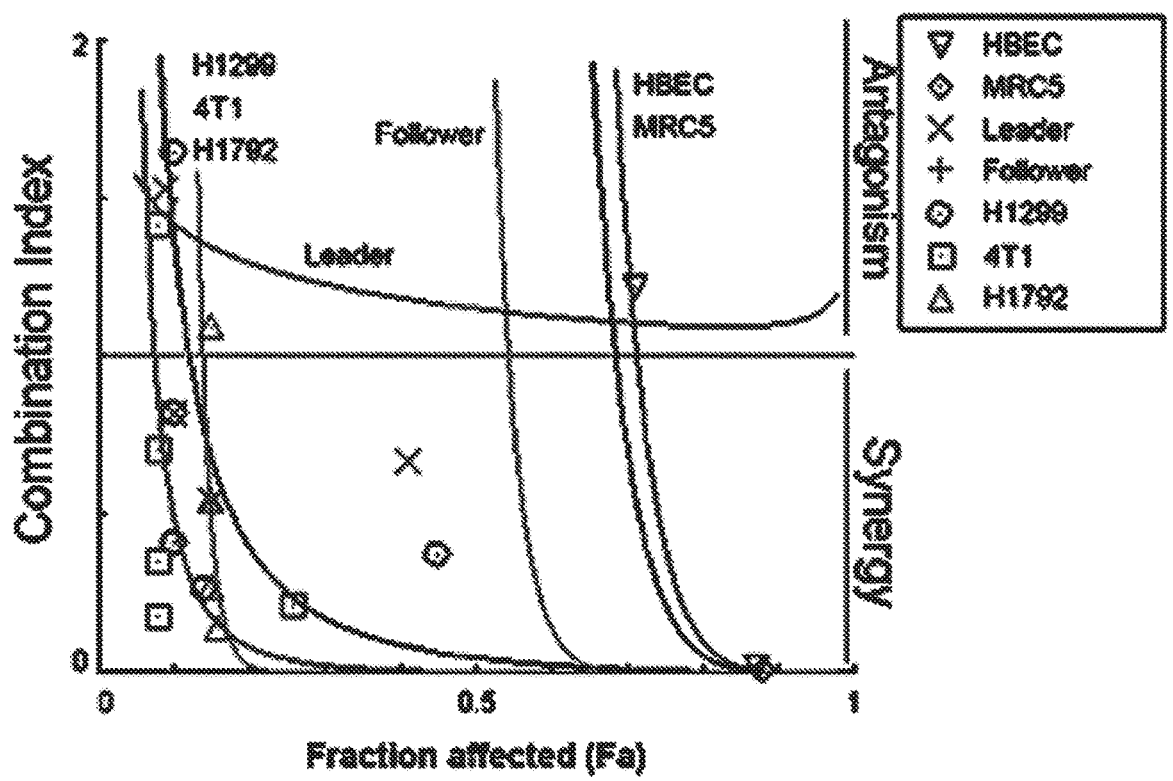
FIG. 8A shows data indicating alexidine dihydrochloride and Bay-876 co-target metabolic heterogeneity to inhibit collective invasion. Combination indexes were obtained for parental lung and breast cancer cell lines (H1299, H1792, 4T1), lung subpopulation cell lines (follower and leader cells), and normal lung epithelial cells and lung fibroblasts (HBEC, MRC5) using a 72-hour SRB assay for cell viability.
Figure 8B:
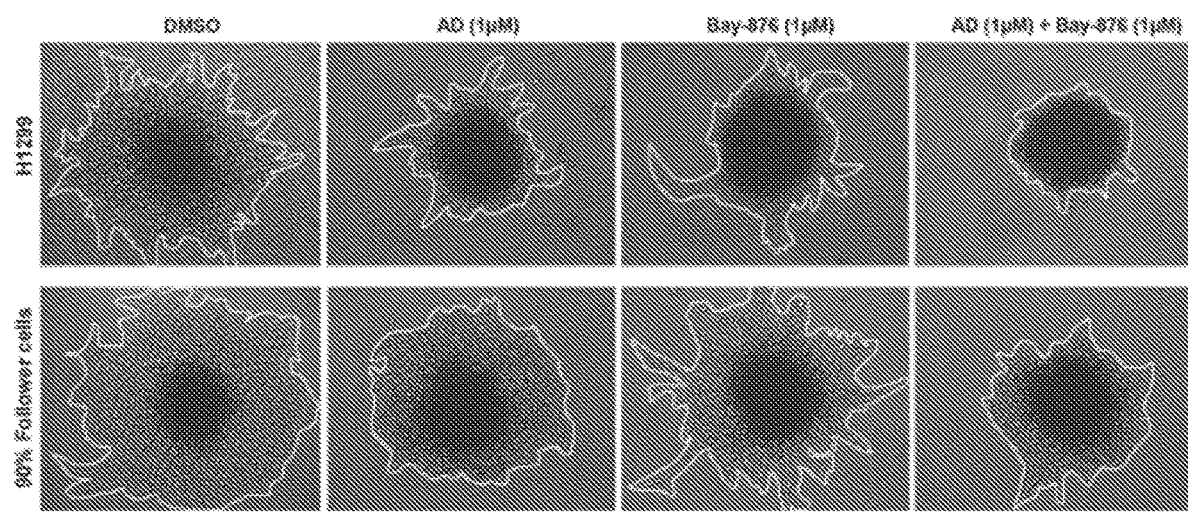
FIG. 8B shows cell spheroids that were embedded in Matrigel™ with either DMSO, alexidine, Bay-876, or alexidine plus Bay-876 and allowed to invade for 24 hours. Brightfield representative images are shown. Solid lines designate outer perimeter. Scale bar=50 μm.
Figure 8C:
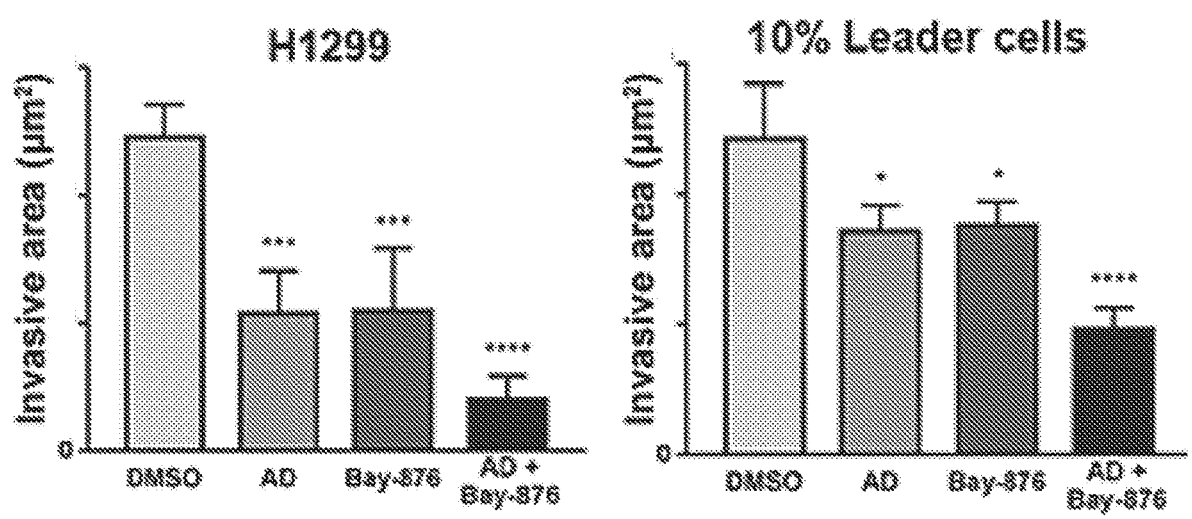
FIG. 8C shows data on the quantification of invasive areas using conditions shown in FIG. 8B.

Alexidine treatment for 24 hours causes increased lactate production and increased p-PDHS293. There is no significant impact on pPDHS293 in follower cells. Since alexidine inhibits active PDH in leaders and Bay-876 targets GLUT1, the combination of alexidine and Bay-876 to co-target these cellular subtypes, respectively, during collective invasion was examined. To quantitatively determine synergy a combination index analyses was used. Alexidine and Bay-876 exhibit greater synergism in parental cell lines (H1299, 4T1, H1792) than in the individual leader or follower subtypes alone (FIG. 8A). Importantly, normal lung epithelial cells (HBEC, MRC5) had no synergy at low and moderate doses (FIG. 8A). The effects of Bay-876 plus alexidine on invasion were examined. Data indicates that the combination inhibited collective invasion more than either compound alone across multiple lung and mixed leader:follower lines (FIGS. 8B and 8C). Taken together, these results indicate a therapeutic strategy of co-targeting PDH and GLUT1 for inhibiting the collective invasion of heterogenous cellular subtypes. It is also contemplated that one can co-target metabolically heterogeneous populations using the combination of the leader cell targeting agent, alexidine, and the GLUT1 targeting agent, BAY-876 or the glycolytic/PPP activity of followers and OXHOS-driven biology of the leaders in a manor illustrated in the table below.

| Table illustrating classes of agents that can be combined from Group A and B | |
|---|---|
| A. Follower/Proliferating: glycolysis/PPP targeting agent | B. Leader/Invasive: MPC, PDH, electron transport chain |
| 1. YAP/TEAD inhibitor (that targets GLUT1): verteporfin | 1. PDHE1a inhibitor -Alexidine or CPI-613, |
| 2. GLUT1 inhibitor: BAY-876 | 2. Complex I inhibitors |
| 3. G6PD inhibitor: 6AN | 3. Mitochondrial pyruvate carrier inhibitor-UK-5099 |
| 4. ERK inhibitor - GDC | |

The invention claimed is:

1. A method of treating small cell lung cancer comprising administering to a human subject in need thereof a combination of chemotherapy agents, wherein a first chemotherapy agent is alexidine, alexidine derivative, or salt thereof, and a second chemotherapy agent is N4-[1-[(4-cyanophenyl)methyl]-5-methyl-3-(trifluoromethyl)-1H-pyrazol-4-yl]-7-fluoro-2,4-quinolinedicarboxamide or salt thereof;
wherein the alexidine derivative is selected from 1-(2-ethylhexyl)-5-propylbiguanidine, 1,1'-(hexane-1,6-diyl)bis(5-(2-ethylhexyl)biguanidine), 1,1'-(butane-1,4-diyl)bis(5-(2-ethylhexyl)biguanidine), 1,1'-(octane-1,8-diyl)bis(5-(2-ethylhexyl)biguanidine), 1,1'-(hexane-1,6-diyl)bis(5-(2-butylhexyl)biguanidine), 1,1'-(hexane-1,6-diyl)bis(5-(2-ethylbutyl)biguanidine) (TG-AX7), 1,1'-(hexane-1,6-diyl)bi(5-(4-methoxybutyl)biguanidine).

2. A method of treating non-small cell lung cancer comprising administering to a human subject in need thereof a combination of chemotherapy agents, wherein a first chemotherapy agent is alexidine, alexidine derivative, or salt thereof, and a second chemotherapy agent is N4-[1-[(4-cyanophenyl)methyl]-5-methyl-3-(trifluoromethyl)-1H-pyrazol-4-yl]-7-fluoro-2,4-quinolinedicarboxamide or salt thereof;
wherein the alexidine derivative is selected from 1-(2-ethylhexyl)-5-propylbiguanidine, 1,1'-(hexane-1,6-diyl)bis(5-(2-ethylhexyl)biguanidine), 1,1'-(butane-1,4-diyl)bis(5-(2-ethylhexyl)biguanidine), 1,1'-(octane-1,8-diyl)bis(5-(2-ethylhexyl)biguanidine), 1,1'-(hexane-1,6-diyl)bis(5-(2-butylhexyl)biguanidine), 1,1'-(hexane-1,6-diyl)bis(5-(2-ethylbutyl)biguanidine) (TG-AX7), 1,1'-(hexane-1,6-diyl)bi(5-(4-methoxybutyl)biguanidine).

\* \* \* \* \*